| United States Patent [19] | [11] Patent Number: 4,494,978 |
| Chan | [45] Date of Patent: * Jan. 22, 1985 |

[54] HERBICIDAL N-(N'-HYDROCARBYLOXYCARBAMYLALKYL)-2,6-DIALKYL-ALPHA-HALOACETANILIDES

[75] Inventor: David C. K. Chan, San Francisco, Calif.

[73] Assignee: Chevron Research Company, San Francisco, Calif.

[*] Notice: The portion of the term of this patent subsequent to Mar. 16, 1993 has been disclaimed.

[21] Appl. No.: 755,883

[22] Filed: Dec. 30, 1976

[51] Int. Cl.³ ............................................. A01N 37/22
[52] U.S. Cl. ........................................... 71/117; 71/88; 544/63; 548/240; 260/453 RW; 260/455 R
[58] Field of Search ................... 260/453 RW; 71/118

[56] References Cited

U.S. PATENT DOCUMENTS

| 3,634,509 | 1/1972 | Yates et al. | 260/453 RW |
| 3,723,474 | 3/1973 | Teach et al. | 260/453 RW |
| 3,780,090 | 12/1973 | Akiba et al. | 71/111 X |
| 3,829,306 | 8/1974 | Ratts | 71/76 |
| 3,856,860 | 12/1974 | Maravetz | 71/118 |
| 3,944,607 | 3/1976 | Chan | 71/118 X |
| 3,997,326 | 12/1976 | Chan | 71/118 |
| 4,008,066 | 2/1977 | Moser | 71/118 |
| 4,126,440 | 11/1978 | Moser et al. | 260/453 RW X |
| 4,200,451 | 4/1980 | Vogel et al. | 71/118 |
| 4,205,168 | 5/1980 | Chan | 546/226 X |

*Primary Examiner*—Joseph Paul Brust
*Attorney, Agent, or Firm*—S. R. LaPaglia; T. G. DeJonghe; L. S. Squires

[57] ABSTRACT

N-(N'-hydrocarbyloxycarbamylalkyl)-2,6-dialkyl-alpha-haloacetanilides have herbicidal activity, particularly in preemergent applications.

7 Claims, No Drawings

HERBICIDAL N-(N'-HYDROCARBYLOXYCARBAMYLALKYL)-2,6-DIALKYL-ALPHA-HALOACETANILIDES

CROSS-REFERENCE TO RELATED APPLICATION

This application is related to Applicant's copending application Ser. No. 660,086, filed Feb. 23, 1976, now U.S. Pat. No. 3,997,326, which is directed to herbicidal N-(N'-alkynylcarbamylmethyl)-2,6-dialkyl-alpha-haloacetanilides.

BACKGROUND OF THE INVENTION

U.S. Pat. No. 3,780,090 of Akiba et al and Belgian Pat. No. 796,263 of Hercules disclose the use of alkyl alpha-(n-haloacetyl-N-2,6-dialkyl phenylamino) alkanoate esters as herbicides. German Offen. No. 2,350,944 of Ciga Geigy discloses alpha-(N-haloacetyl-N-2,6-dialkylphenylamino) alkanoate esters as antifungal agents. Belgian Pat. No. 813,469 of Ciba Geigy discloses the use of phenylamine acetamides as herbicides.

DESCRIPTION OF THE INVENTION

The N-(N'-hydrocarbyloxycarbamylalkyl)-2,6-dialkyl-alpha-haloacetanilide compounds of the invention are represented by the formula (I):

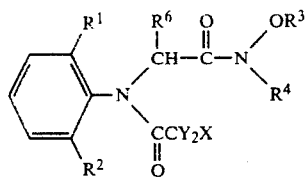

wherein $R^1$ and $R^2$ individually are alkyl groups of 1 to 6 carbon atoms; $R^3$ is hydrogen, alkyl of 1 to 6 carbon atoms, haloalkyl of 1 to 2 carbon atoms and 1 to 4 chlorine or bromine, alkenyl of 3 to 6 carbon atoms, alkynyl of 3 to 6 carbon atoms, or phenyl or benzyl substituted with up to 2 fluoro, chloro, bromo or alkyl of 1 to 3 carbon atoms; $R^4$ is hydrogen, alkyl of 1 to 6 carbon atoms, haloalkyl of 1 to 2 carbon atoms and 1 to 4 chlorine or bromine, alkenyl of 3 to 6 carbon atoms, alkynyl of 3 to 6 carbon atoms, or phenyl or benzyl substituted with up to 2 fluoro, chloro, bromo or alkyl of 1 to 3 carbon atoms, with the proviso that together $R^3$ and $R^4$ may form a divalent alkylene moiety of 3 to 6 carbon atoms; $R^6$ is hydrogen or alkyl of 1 to 6 carbon atoms; X is fluorine, chlorine, bromine or iodine; and Y individually is hydrogen, fluorine, chlorine, bromine or iodine.

Representative alkyl groups which $R^1$, $R^2$, $R^3$, $R^4$ and $R^6$ may represent include methyl, ethyl, propyl, isopropyl, butyl, sec-butyl, t-butyl, pentyl, isohexyl, etc. Representative haloalkyl groups which $R^3$ and $R^4$ may represent include chloromethyl, dichloromethyl, tribromomethyl and tetrachloroethyl. Representative alkenyl groups which $R^3$ and $R^4$ may represent include allyl, 1-propenyl, 2-butenyl, etc. Representative alkynyl groups which $R^3$ and $R^4$ may represent include propargyl, 2-butynyl, 3-pentynyl, etc. Representative substituted-benzyl and substituted-phenyl groups which $R^3$ and $R^4$ may represent include 4-fluorophenyl, 2,4-dichlorophenyl, p-tolyl, 4-methylbenzyl, 4-chlorobenzyl, 2,4-dibromobenzyl, etc. Representative divalent alkylene groups, formed by joining $R^3$ and $R^4$ include trimethylene, 2-methyltrimethylene, tetramethylene and 2-methyltetramethylene.

Preferably $R^1$ is alkyl of 1 to 3 carbon atoms, $R^2$ is alkyl of 1 to 3 carbon atoms, $R^3$ is hydrogen, alkyl of 1 to 3 carbon atoms, 2-alkenyl, 2-alkynyl, or benzyl, $R^4$ is hydrogen or alkyl of 1 to 3 carbon atoms, $R^6$ is hydrogen or alkyl of 1 to 3 carbon atoms, X is chlorine or bromine and Y is hydrogen. When $R^3$ and $R^4$ are joined to form a divalent alkylene moiety, the divalent alkylene moiety preferably is trimethylene or tetramethylene.

A preferred class of compounds represented by formula (I) is that wherein $R^1$ is alkyl of 1 to 3 carbon atoms, $R^2$ is alkyl of 1 to 3 carbon atoms, $R^3$ is alkyl of 1 to 3 carbon atoms, $R^4$ is hydrogen or alkyl of 1 to 3 carbon atoms, $R^6$ is hydrogen, X is chlorine or bromine and Y is hydrogen.

Representative compounds of formula (I) are:
N-(N'-ethoxycarbamylmethyl)-2,6-dimethyl-alpha-dichloroacetanilide
N-(N'-phenoxy-N'-methylcarbamylmethyl)-2,6-diethyl-alpha-chloroacetanilide
N-[(1-N'-chloromethoxycarbamyl)ethyl]-2,6-dimethyl-alpha-chloroacetanilide
N-(N'-4-chlorobenzyloxycarbamylmethyl)-2,6-isopropyl-alpha-bromoacetanilide
N-(N'-2-butenyloxycarbamylmethyl)-2,6-dimethyl-alpha-fluoroacetanilide
N-(isoxazolidinylcarbonylmethyl)-2,6-dimethyl-alpha-bromoacetanilide
N-(tetrahydro-1,2-oxazinylcarbonylmethyl)-2,6-dimethyl-alpha-iodoacetanilide and
N-(N'-hydroxycarbamylmethyl)-2-methyl-6-ethyl-alpha-chloroacetanilide.

The compounds of the invention may be prepared by: (1) alkylating an aniline compound (II) with an alkyl alpha-halothioalkanoate (III) and; (2) reacting the resulting alpha-(N-phenylamino)thioalkanoate (IV) with an amine (V) in the liquid phase to produce the N-carbamylalkyl-2,6-dialkylaniline intermediate (VI); and (3) subsequently acylating the N-carbamylalkyl-2,6-dialkylphenylamine (VI) with an alpha-haloacetyl halide (VII) to give the N-carbamylalkyl-2,6-dialkyl-alpha-halo-acetanilide product (I). This sequence of reactions is depicted by the following equations:

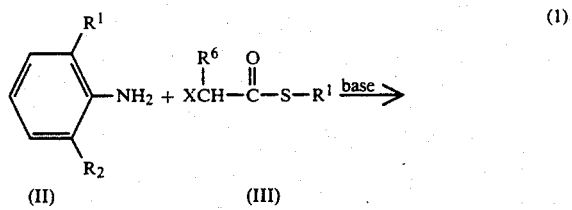

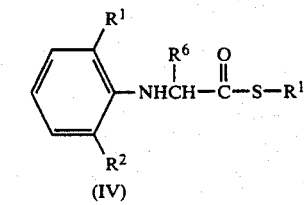

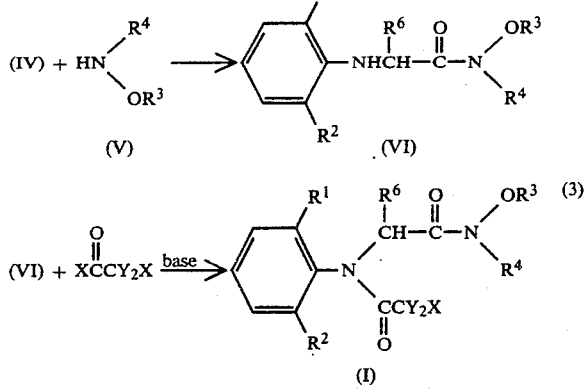

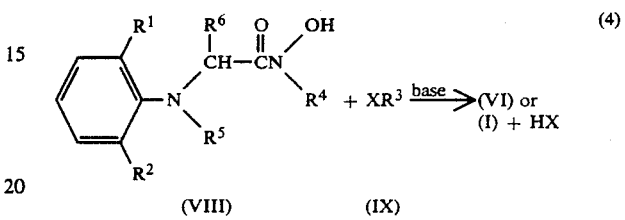

wherein $R^1$, $R^2$, $R^3$, $R^4$, $R^6$, Y and X have the same significance as previously defined.

The alkylation reaction (1) is conducted in the presence of a base. Suitable bases are inorganic alkali metal carbonates such as sodium carbonate or potassium carbonate. Generally, substantially equimolar amounts of reactants (II) and (III) and the base are employed. The reaction is conducted in inert polar organic solvents, e.g., apolar diprotic solvents such as dimethylformamide and acetonitrile, at reaction temperatures varying from 0° C. to 90° C., preferably from 20° C. to 50° C. The reaction pressure may be atmospheric, subatmospheric, or superatmospheric. However, for convenience of conducting the reaction, the pressure is generally atmospheric. The reaction time will, of course, vary depending upon the reactants and the reaction temperature. Generally the reaction time is from 0.25 to 24 hours. The product (IV) is generally purified by conventional procedures, e.g., extraction, distillation or crystallization, before use in the amidation reaction (2).

In reaction (1) the thioalkanoate ester (II) is preferably a lower alkyl alpha-halothioacetate, i.e., $R^1$ is alkyl of 1 to 3 carbon atoms and $R^6$ is hydrogen.

Reaction (2) is preferably conducted in an inert liquid diluent. Suitable diluents include water, organic solvents, e.g., apolar diprotic solvents such as dimethylformamide and acetonitrile, and mixtures of water and organic solvents. Generally, substantially equimolar amounts of the thioacetate ester (IV) and the amine (V) are employed, although an excess of the amine may be employed. The reaction temperatures vary from 0° to 100° C. and the reaction pressure may be atmospheric, subatmospheric or superatmospheric. The reaction time will, of course, vary depending upon the reactants and the reaction temperature. Generally, the reaction time is 0.25 to 24 hours. To decrease the reaction time, the reaction may be conducted in the presence of an organic base such as a pyridine compound or a trialkylamine. Suitable pyridine compounds include pyridine, alpha-picoline, 3,5-dimethylpyridine, etc., and suitable trialkylamines include trimethylamine, tributylamine, etc. When a base is employed, amounts of base from about 0.01 to 1 mol per mol of thioalkanoate ester are generally satisfactory.

The acylation reaction (3) is conducted by conventional procedures in the presence of an organic base such as a trialkyl amine or a pyridine compound. The reactants (VI) and (VII) and the base are generally contacted in substantially equimolar amounts in an inert organic solvent at a temperature of 0° C. to 50° C. Suitable inorganic solvents include ethyl acetate, methylene chloride, dimethoxyethane, benzene, etc. The product is isolated and purified by conventional procedures such as extraction, distillation, crystallization, etc.

The N-(N'-hydrocarbyloxycarbamylalkyl)-2,6-dialkylaniline intermediate (VI) or the product (I) may also be prepared by alkylating an N-(N'-hydroxycarbamylalkyl)-2,6-dialkylaniline or 2,6-alpha-haloacetanilide (VIII) with a halide compound of the formula $XR^3$ (IX), as depicted by the following reaction:

wherein $R^1$, $R^2$ and $R^4$ have the same significance as previously defined, $R^3$ is alkyl, alkenyl, alkynyl, benzyl or substituted-benzyl, and $R^5$ is hydrogen or haloacetyl of 1 to 3 halo groups selected from fluoro, chloro or bromo (i.e., $-COCY_2X$ in formula I).

The alkylation reaction (4) is conducted by conventional procedures similar to that described for reaction (1). In reaction (4), an alkali metal hydroxide is generally preferred as the base. Generally, substantially equimolar amounts of the reactants (VIII) and (IX) and the base are employed. Preferably reaction (4) is conducted in the presence of catalytic amounts of a quaternary ammonium salt. Generally, amounts of quaternary ammonium salt per mol of the reactant (VIII) vary from about 0.01 to 0.3, although amounts from 0.05 to 0.02 mol per mol of the reactant (VIII) are preferred. Suitable quaternary ammonium salts are tetraalkylammonium halides wherein the alkyl has 1 to 6 carbon atoms and the halide is fluoro, chloro, bromo or iodo, e.g., tetramethaneammonium chloride or tetrabutylammonium chloride.

Compounds wherein $R^3$ and $R^4$ are joined to form a divalent alkylene group may be prepared according to reaction (4) by employing reactant (VIII) with $R^5$ equal to hydrogen and a 1,3-diiodoalkane or 1,4-diiodoalkane as the halide reactant (IX).

EXAMPLES

EXAMPLE 1

Preparation of ethyl alpha-(N-2-methyl-6-ethylphenylamino)thioacetate

A slurry of 24.2 g (0.2 mol) ethyl alpha-bromothio acetate, 36.8 g (0.2 mol) 2-methyl-6-ethylaniline and 2.2 g (0.2 mol) sodium carbonate in 200 ml dimethylformamide was stirred at 25° C. for 5 days. The reaction mixture was diluted with about 25 ml water and extracted with benzene. The benzene extracts were washed with water, dried over magnesium sulfate and evaporated under reduced pressure to give 48.2 g of ethyl alpha-(N-2-methyl-6-ethylphenylamino)thioacetate.

EXAMPLE 2

Preparation of
N-(N'-methoxycarbamylmethyl)-2,6-dimethylaniline

A solution of 33.4 g (0.15 mol) ethyl alpha-(2,6-dimethylphenylamino)thioacetate, 12.5 g (0.15 mol) methoxyamine hydrochloride and 8 g of a 50% aqueous sodium hydroxide solution (0.1 mol NaOH) in 200 ml acetonitrile was heated under reflux for 16 hours. The reaction mixture was filtered and the filtrate evaporated under reduced pressure to give an oil residue. The residue was chromatographed on a silica gel column. Elution with 80% ethyl ether/20% hexane gave the product as an oil (7.5 g). The product and its elemental analysis are tabulated in Table I as Compound No. 1.

EXAMPLE 3

Preparation of
N-(N'-methoxycarbamylmethyl)-2,6-dimethyl-alpha-chloroacetanilide A 2.44 g (0.022 mol) sample of chloroacetyl chloride was added dropwise to a solution of 4.5 g (0.022 mol) N-(N'-methoxycarbamylmethyl)-2,6-dimethylaniline and 1.73 g (0.022 mol) pyridine in 150 ml dichloromethane. The reaction was stirred for 2 hours at about 25° C., washed successively with water, aqueous sodium bicarbonate, water, dried over magnesium sulfate and evaporated under reduced pressure to a crystalline residue. The residue was washed with ethyl ether/hexane and dried to give 5.4 g of the product, as a greyish solid, m.p. 122°–125° C. The product and its elemental analysis are tabulated in Table I as Compound No. 2.

EXAMPLE 4

Preparation of
N-(N'-hydroxycarbamylmethyl)-2,6-dimethylaniline

A solution of 101 g 50% aqueous sodium hydroxide (1.26 mol NaOH) and 100 ml of water was added slowly to a cooled solution (ice bath) of 210 g (1 mol) methyl alpha-(2,6-dimethylphenylamino)thioacetate and 87.6 g (1.26 mol) hydroxylamine hydrochloride in 1500 ml methanol. After completion of the addition, the reaction mixture was stirred about 40 hours at 25° C. and then evaporated under reduced pressure to give a solid residue. The residue was washed with water to give a tan solid. The tan solid was washed with water and 80% petroleum ether/20% ethyl ether. The solid was dried to give 57.2 g of the product, m.p. 89° C. Elemental analysis for $C_{10}H_{14}N_2O_2$ showed: %C, calc. 61.8, found 62.0; %H, calc. 7.3, found 7.3; %N, calc. 14.4, found 14.4.

EXAMPLE 5

Preparation of
N-(N'-allyloxycarbamylmethyl)-2,6-dimethylaniline

A solution of 8 g 50% aqueous sodium hydroxide (0.1 mol NaOH) was added dropwise to a solution of 19.4 g (0.1 mol) N-(N'-hydroxycarbamylmethyl)-2,6-dimethylaniline, 12.1 g (0.1 mol) allyl bromide and 4 g methyl tricaprylammonium chloride in 100 ml N,N-dimethylformamide. The reaction mixture was stirred for about 2 hours, diluted with ice water, and extracted with benzene. The benzene extracts were washed with water, dried over magnesium sulfate and evaporated under reduced pressure to give a dark oil. The product was separated from the oil by column chromatography on silica gel with mixtures of petroleum ether/diethyl ether as eluants. The product (12.8 g) was a colorless solid, m.p. 52°–53° C. The product and its elemental analysis are tabulated in Table I as Compound No. 5.

EXAMPLE 6

Preparation of
N-(N'-allyloxycarbamylmethyl)-2,6-dimethyl-alpha-chloroacetanilide A 5.2 g (0.046 mol) sample of chloroacetyl chloride was added slowly at 25° C. to a solution of 9.7 g (0.041 mol) N-(N'-allyloxycarbamylmethyl)-2,6-dimethylaniline and 3.6 g (0.046 mol) pyridine in 125 ml ethyl acetate. The reaction mixture was then stirred for 2 hours and diluted with water. The organic phase was separated, washed with saturated aqueous sodium bicarbonate solution, washed with water, dried over magnesium sulfate and evaporated under reduced pressure to give a solid residue. The solid was slurried with ethyl ether/petroleum ether at 0° C. and dried to give 11.7 g of the product as a colorless solid, m.p. 106°–107° C. The product and its elemental analysis are tabulated in Table I as Compound No. 6.

EXAMPLE 7

Preparation of
N-(N'-propargyloxycarbamylmethyl)-2,6-dimethylaniline and
N-(N'-propargyl-N'-propargyloxycarbamylmethyl)-2,6-dimethylaniline A solution of 19.4 g (0.1 mol) N-(N'-hydroxycarbamylmethyl)-2,6-dimethylaniline, 11.9 g (0.1 mol) propargyl bromide, 8 g 50% aqueous sodium hydroxide (0.1 mol NaOH) and 4 g methyl tricaprylammonium chloride in 100 ml N,N-dimethylformamide was stirred at ambient temperature for about 2 hours. The reaction mixture was then diluted with water and extracted with benzene. The benzene extracts were washed with water, dried over magnesium sulfate and evaporated under reduced pressure to give an oil. The oil was chromatographed on a silica gel column with mixtures of petroleum ether/ethyl ether as eluants.

A 3.2-g sample of N-(N'-propargyl-N'-propargyloxycarbamylmethyl)-2,6-dimethylaniline was eluted from the column with 60% petroleum ether/40% ethyl ether, and a 10.8 g sample of N-(N'-propargyloxycarbamylmethyl)-2,6-dimethylaniline was eluted from the column with 40% petroleum ether/60% ethyl ether. These products are tabulated in Table I as Compound Nos. 7 and 9.

EXAMPLE 8

Preparation of
N-(N'-propargyloxycarbamylmethyl)-2,6-dimethyl-alpha-chloroacetanilide A 4.0-g (0.0353 mol) sample of chloroacetyl chloride was added dropwise at about 25° C. to a stirred solution of 8.2 g (0.0353 mol) N-(N'-propargyloxycarbamylmethyl)-2,6-dimethylaniline and 2.8 g (0.0353 mol) pyridine in 125 ml ethyl acetate. The reaction mixture was stirred at 25° C. for about 2 hours, diluted with water and extracted with dichloromethane. The dichloromethane extracts were washed with water, saturated aqueous sodium bicarbonate, dried over magnesium sulfate and evaporated under reduced pressure to give a soid residue. The solid was slurried with ethyl ether/petroleum ether at 0° C., filtered and dried to give the product as a colorless solid, m.p. 144°–145° C. The product and its elemental analysis are tabulated in Table I as Compound No. 8.

EXAMPLE 9

Preparation of N-(N'-benzyloxycarbamylmethyl)-2,6-dimethylaniline

A solution of 8 g 50% aqueous sodium hydroxide (0.1 mol NaOH) and 50 ml water was added dropwise to a stirred solution of 19.4 g (0.1 mol) N-(N'-hydroxycarbamylmethyl)-2,6-dimethylaniline and 17.1 g (0.1 mol) benzyl bromide in 200 ml N,N-dimethylformamide. The reaction mixture was stirred for about 16 hours, diluted with ice water and extracted with benzene. The benzene solution was washed with water, dried over magnesium sulfate and evaporated under reduced pressure at 45° C. to give an oily residue. The oil was placed on a silica gel chromatography column and eluted with mixtures of petroleum ether/ethyl ether. The last compound eluted from the column (with 40% petroleum ether/60% ethyl ether) was identified by nuclear magnetic resonance (NMR) analysis as the desired product (15.6 g). The product and its elemental analysis are tabulated in Table I as Compound No. 11.

A small amount of N-(N'-benzyl-N'-benzyloxycarbamylmethyl)-2,6-dimethylaniline (2.6 g) was also eluted from the column with 50% petroleum ether/50% ethyl ether.

EXAMPLE 10

Preparation of N-(N'-benzyloxycarbamylmethyl)-2,6-dimethyl-alpha-chloroacetanilide A 5.08-g (0.045 mol) sample of chloroacetyl chloride was added over 15 minutes to a solution of 11.7 g (0.041 mol) N-(N'-benzyloxycarbamylmethyl)-2,6-dimethylaniline and 3.6 g (0.045 mol) pyridine in 200 ml ethyl acetate. The reaction mixture was stirred for 2 hours, washed with water, washed with saturated aqueous sodium bicarbonate, washed with water, dried over magnesium sulfate and evaporated under reduced pressure at 50° C. to give a solid residue. The residue was slurried at 0° C. with ethyl ether/petroleum ether, filtered and dried to give 12.8 g of the product, as a colorless solid, m.p. 115°–116° C. The product and its elemental analysis are tabulated in Table I as Compound No. 12.

EXAMPLE 11

Preparation of N-(isoxazolidinylcarbonylmethyl)-2,6-dimethylaniline

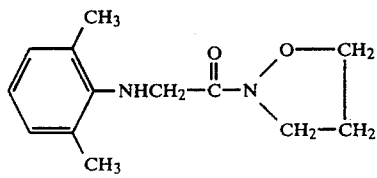

A solution of 16 g 50% aqueous sodium hydroxide (0.2 mol NaOH) and 10 ml water was added slowly to a solution of 19.4 g (0.1 mol) N-(N'-hydroxycarbamylmethyl)-2,6-dimethylaniline, 30 g (0.1 mol) 1,3-diiodopropane and 4 g benzyl triethylammonium chloride in 250 ml N,N-dimethylformamide. The reaction mixture was then stirred for 2 days at 25° C., diluted with 500 ml ice water, acidified to pH 6 with glacial acetic acid, and extracted with benzene. The benzene extracts were washed with water, dried over magnesium sulfate and evaporated under reduced pressure to give a tan oil, which crystallized on standing. The crystallized material was washed with cold ethyl ether and petroleum ether to give the product, m.p. 82°–83° C. The product and its elemental analysis are tabulated in Table I as Compound No. 17.

EXAMPLE 12

Preparation of (N-isoxazolidinylcarbonylmethyl)-2,6-dimethyl-alpha-chloroacetanilide

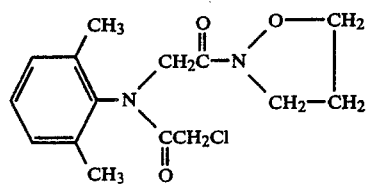

A solution of 3.5 g (0.031 mol) chloroacetyl chloride in 5 ml ethyl acetate was added dropwise at 25° C. to a solution of 7 g (0.0299 mol) N-(isoxazolidinylcarbonylmethyl)-2,6-dimethylaniline and 2.5 g (0.031 mol) pyridine in 100 ml ethyl acetate. The reaction mixture was stirred for 1 hour, washed with water, washed with saturated sodium bicarbonate (a solid separated) and diluted with dichloromethane (to dissolve solid). The organic phase was separated, washed with water, dried over magnesium sulfate and evaporated under reduced pressure to give a solid. The solid was triturated with ethyl ether and dried to give the product, as a colorless solid, m.p. 146°–147° C. The product and its elemental analysis are tabulated in Table I as Compound No. 18.

The compounds tabulated in Table I were prepared by procedures similar to those described in Examples 1-12. The structure of each compound tabulated in Table I was confirmed by NMR spectroscopy and/or infrared spectral analysis.

UTILITY

The compounds of the present invention are herbicidal in both pre- and post-emergent applications. For pre-emergent control of undesirable vegetation, the herbicidal compounds will be applied in herbicidally effective amounts to the locus or growth medium of the vegetation, e.g., soil infested with seeds and/or seedlings of such vegetation. Such application will inhibit the growth of or kill the seeds, germinating seeds and seedlings. For post-emergent applications, the herbicidal compounds will be applied directly to the foliage and other plant parts. Generally, the herbicidal compounds of the invention are effective against weed grasses as well as broadleaved weeds. The compounds are particularly effective as pre-emergent herbicides against broadleaved and grass weeds, with little or no phytotoxicity to crops such as oats, sorghum, cotton and peas.

The compounds of the present invention can be used alone as herbicides. However, it is generally desirable to apply the compounds in herbicidal compositions comprising one or more of the herbicidal compounds intimately admixed with a biologically inert carrier. The carrier may be a liquid diluent or a solid, e.g., in the form of dust powder or granules. In the herbicidal composition, the active herbicidal compounds can be from about 0.01 to 95% by weight of the entire composition.

Suitable liquid diluent carriers include water and organic solvents, e.g., hydrocarbons such as benzene, toluene, kerosene, diesel oil, fuel oil, and petroleum naphtha. Suitable solid carriers are natural clays such as kaolinite, atalpulgite and montmorillonite. In addition, talcs, pyrophillite, diatomaceous silica, synthetic fine silicas, calcium aluminosilicate and tricalcium phosphate are suitable carriers. Organic materials such as walnut-shell flour, cottonseed hulls, wheat flour, wood flour or redwood-bark flour may also be used as solid carriers.

The herbicidal composition will also usually contain a minor amount of a surface-active agent. Such surface agents are those commonly known as wetting agents, dispersing agents and emulsifying agents, and can be anionic, cationic or nonionic in character. The herbicidal compositions may also contain other pesticides, adjuvants, stabilizers, conditioners, fillers, and the like.

The amount of herbicidal compound or composition administered will vary with the particular plant part or plant growth medium which is to be contacted, the general location of application—i.e., sheltered areas such as greenhouses, as compared to exposed areas such as fields—as well as the desired type of control. Generally, for both pre- and post-emergent control, the herbicidal compounds of the invention are applied at rates of 0.2 to 60 kg/ha, and the preferred rate is in the range 0.5 to 40 kg/ha.

Pre-emergent herbicidal tests on representative compounds of the invention were made using the following method:

Pre-Emergent Test

An acetone solution of the test compound was prepared by mixing 750 mg of the compound, 220 mg of a nonionic surfactant and 25 ml of acetone. This solution was added to approximately 125 ml of water containing 156 mg of surfactant.

Seeds of the test vegetation were planted in a pot of soil and the test solution was sprayed uniformly onto the soil surface at a dose of 33 micrograms/cm$^2$. The pot was watered and placed in a greenhouse. The pot was watered intermittently and was observed for seedling emergence, healt of emerging seedlings, etc., for a 3-week period. At the end of this period, the herbicidal effectiveness of the compound was rated based on the physiological observations. A 0-to-100 scale was used, 0 representing no phytotoxicity, 100 representing complete kill. The results of these tests appear in Table II.

TABLE I

Compounds of the formula 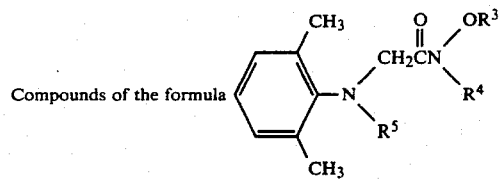

| Compound No. | $R^3$ | $R^4$ | $R^{5(a)}$ | Melting Point, °C. | Elemental Analysis Calc. | | Found |
|---|---|---|---|---|---|---|---|
| 1 | CH$_3$ | H | H | oil | 63.5 | (C) | 64.3 |
|  |  |  |  |  | 7.8 | (H) | 7.4 |
|  |  |  |  |  | 13.5 | (N) | 14.4 |
| 2 | CH$_3$ | H | COCH$_2$Cl | 122–125 | 12.5 | (Cl) | 11.8 |
| 3 | CH$_3$ | CH$_3$ | H | oil | 64.9 | (C) | 62.8 |
|  |  |  |  |  | 8.2 | (H) | 7.9 |
|  |  |  |  |  | 12.6 | (N) | 12.4 |
| 4 | CH$_3$ | CH$_3$ | COCH$_2$Cl | 105–107 | 11.9 | (Cl) | 12.1 |
| 5 | CH$_2$CH=CH$_2$ | H | H | 52–53 | 66.4 | (C) | 65.0 |
|  |  |  |  |  | 7.7 | (H) | 7.5 |
|  |  |  |  |  | 12.0 | (N) | 11.7 |
| 6 | CH$_2$CH=CH$_2$ | H | COCH$_2$Cl | 106–107 | 11.4 | (Cl) | 11.5 |
| 7 | CH$_2$C≡CH | H | H | oil | 67.2 | (C) | 66.4 |
|  |  |  |  |  | 6.9 | (H) | 6.6 |
|  |  |  |  |  | 12.1 | (N) | 11.8 |
| 8 | CH$_2$C≡CH | H | COCH$_2$Cl | 144–145 | 11.5 | (Cl) | 11.6 |
| 9 | CH$_2$C≡CH | CH$_2$C≡CH | H | oil | — | — | — |
| 10 | CH$_2$C≡CH | CH$_2$C≡CH | COCH$_2$Cl | oil | 10.2 | (Cl) | 12.2 |
| 11 | φCH$_2$ | H | H | oil | 71.8 | (C) | 71.9 |
|  |  |  |  |  | 7.1 | (H) | 7.2 |
|  |  |  |  |  | 9.9 | (N) | 9.6 |
| 12 | φCH$_2$ | H | COCH$_2$Cl | 115–116 | 9.8 | (Cl) | 9.8 |
| 13 | H | CH$_3$ | H | 107–108 | 63.5 | (C) | 64.1 |
|  |  |  |  |  | 7.8 | (H) | 7.6 |
|  |  |  |  |  | 13.5 | (N) | 15.5 |
| 14 | H | CH$_3$ | COCH$_2$Cl | 125–129 | 12.5 | (Cl) | 12.2 |
| 15 | CH$_2$C≡CH | CH$_3$ | H | oil | 68.3 | (C) | 67.6 |
|  |  |  |  |  | 7.4 | (H) | 7.0 |
|  |  |  |  |  | 11.4 | (N) | 11.0 |
| 16 | CH$_2$C≡CH | CH$_3$ | COCH$_2$Cl | 76–77 | 11.0 | (Cl) | 11.4 |
| 17 | $^{(b)}$—CH$_2$CH$_2$CH$_2$— | | H | 82–83 | 66.6 | (C) | 66.5 |
|  |  |  |  |  | 7.7 | (H) | 7.6 |
|  |  |  |  |  | 11.9 | (N) | 11.9 |
| 18 | $^{(b)}$—CH$_2$CH$_2$CH$_2$— | | COCH$_2$Cl | 146–147 | 11.4 | (Cl) | 11.4 |
| 19 | CH$_2$CH=CH$_2$ | CH$_3$ | H | oil | 67.7 | (C) | 65.3 |
|  |  |  |  |  | 8.1 | (H) | 7.5 |
|  |  |  |  |  | 11.3 | (N) | 10.4 |
| 20 | CH$_2$CH=CH$_2$ | CH$_3$ | COCH$_2$Cl | 39–40 | 11.0 | (Cl) | 13.4 |

TABLE I-continued

Compounds of the formula 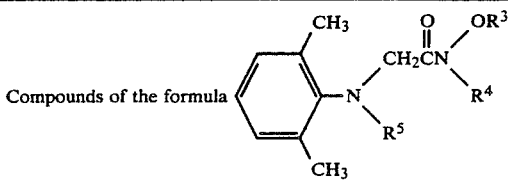

| Compound No. | $R^3$ | $R^4$ | $R^{5(a)}$ | Melting Point, °C. | Elemental Analysis Calc. | | Found |
|---|---|---|---|---|---|---|---|
| 21 | H | H | H | 89 | 61.8 | (C) | 62.0 |
| | | | | | 7.3 | (H) | 7.3 |
| | | | | | 14.4 | (N) | 14.4 |

(a) $R^5$ is hydrogen or haloacetyl of 1 to 3 fluoro, chloro or bromo.
(b) $R^1$ and $R^2$ form —CH$_2$CH$_2$CH$_2$—.
φ = phenyl.

TABLE II

| Compound No. | Herbicidal Effectiveness | | | | | |
|---|---|---|---|---|---|---|
| | L | M | P | C | W | O |
| 2 | 50 | 40 | 60 | 98 | 100 | 98 |
| 4 | 95 | 100 | 100 | 100 | 100 | 95 |
| 6 | 95 | 50 | 50 | 95 | 100 | 45 |
| 8 | 0 | 0 | 0 | 70 | 98 | 35 |
| 10 | 0 | 0 | 0 | 98 | 99 | 60 |
| 12 | 0 | 0 | 0 | 70 | 80 | 0 |
| 14 | 55 | 55 | 35 | 99 | 100 | 95 |
| 16 | 100 | 80 | 100 | 100 | 100 | 83 |
| 18 | 55 | 98 | 95 | 100 | 100 | 100 |
| 20 | 0 | 45 | 0 | 99 | 100 | 90 |

L = Lambsquarter (*Chenopodium album*)
M = Mustard (*Brassica arvensis*)
P = Pigweed (*Amaranthus retroflexus*)
C = Crabgrass (*Digitaria sanguinalis*)
W = Watergrass (*Echinochloa crusgalli*)
O = Wild Oats (*Avena fatua*)

What is claimed is:

1. A method for the control of undesirable vegetation which comprises applying to said vegetation or its habitat a phytotoxic effective amount of a compound having the formula:

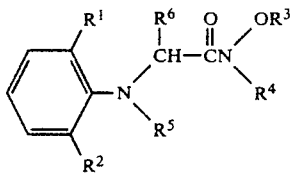

wherein $R^1$ is alkyl of 1 to 6 carbon atoms; $R^2$ is alkyl of 1 to 6 carbon atoms; $R^3$ is alkyl of 1 to 6 carbon atoms, haloalkyl of 1 to 2 carbon atoms and 1 to 4 chlorine or bromine, alkenyl of 3 to 6 carbon atoms, alkynyl of 3 to 6 carbon atoms, phenyl, substituted phenyl having 1 or 2 substituents selected from the group of fluoro, chloro, bromo or alkyl of 1 to 3 carbon atoms, benzyl, or substituted benzyl having 1 or 2 ring substituents selected from the group of fluoro, chloro, bromo or alkyl of 1 to 3 carbon atoms; $R^4$ is hydrogen, alkyl of 1 to 6 carbon atoms, alkenyl of 3 to 6 carbon atoms, alkynyl of 3 to 6 carbon atoms, phenyl, substituted phenyl having 1 or 2 substituents selected from the group of fluoro, chloro, bromo or alkyl of 1 to 3 carbon atoms, benzyl, substituted benzyl having 1 or 2 ring substituents selected from fluoro, chloro, bromo or alkyl of 1 to 3 carbon atoms; and $R^5$ is haloacetyl of 1 to 3 halo groups selected from fluoro, chloro or bromo; $R^6$ is hydrogen or alkyl of 1 to 6 carbon atoms.

2. The method of claim 1 wherein $R^1$ is alkyl of 1 to 3 carbon atoms, $R^2$ is alkyl of 1 to 3 carbon atoms, $R^3$ is alkyl of 1 to 3 carbon atoms, $R^4$ is hydrogen or alkyl of 1 to 3 carbon atoms and $R^5$ is chloroacetyl or bromoacetyl.

3. The method of claim 2 wherein $R^4$ is alkyl of 1 to 3 carbon atoms.

4. The method of claim 3 wherein $R^1$, $R^2$, $R^3$ and $R^4$ are methyl and $R^5$ is chloroacetyl.

5. A herbicidal composition comprising a biologically inert carrier and a phytotoxic effective amount of a compound having the formula:

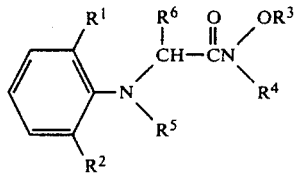

wherein $R^1$ is alkyl of 1 to 6 carbon atoms; $R^2$ is alkyl of 1 to 6 carbon atoms; $R^3$ is alkyl of 1 to 6 carbon atoms, haloalkyl of 1 to 2 carbon atoms and 1 to 4 chlorine or bromine, alkenyl of 3 to 6 carbon atoms, alkynyl of 3 to 6 carbon atoms, phenyl, substituted phenyl having one or two substituents selected from the group of fluoro, chloro, bromo or alkyl of 1 to 3 carbon atoms, benzyl, or substituted benzyl having one or two ring substituents selected from the group of fluoro, chloro, bromo or alkyl of 1 to 3 carbon atoms; $R^4$ is hydrogen, alkyl of 1 to 6 carbon atoms, alkenyl of 3 to 6 carbon atoms, alkynyl of 3 to 6 carbon atoms, phenyl, substituted phenyl having 1 or 2 substituents selected from fluoro, chloro, bromo or alkyl of 1 to 3 carbon atoms, benzyl, or substituted benzyl having 1 or 2 ring substituents selected from fluoro, chloro, bromo or alkyl of 1 to 3 carbon atoms; and $R^5$ is haloacetyl of 1 to 3 halo groups selected from fluoro, chloro or bromo; $R^6$ is hydrogen or alkyl of 1 to 6 carbon atoms.

6. The composition of claim 5 wherein $R^1$ is alkyl of 1 to 3 carbon atoms, $R^2$ is alkyl of 1 to 3 carbon atoms, $R^3$ is alkyl of 1 to 3 carbon atoms, $R^4$ is hydrogen or alkyl of 1 to 3 carbon atoms and $R^5$ is chloroacetyl or bromoacetyl.

7. The composition of claim 6 wherein $R^4$ is alkyl of 1 to 3 carbons atoms.

* * * * *